United States Patent [19]

Heuzé

[11] 4,357,573

[45] Nov. 2, 1982

[54] METHOD OF SURVEYING SUB-SEA PIPELINE

[75] Inventor: Bernard Heuzé, Boulogne, France

[73] Assignee: Societe d'Etudes Contre la Corrosion (SECCO), Boulogne, France

[21] Appl. No.: 116,828

[22] Filed: Jan. 30, 1980

[30] Foreign Application Priority Data

Feb. 1, 1979 [FR] France .................................. 79 02644

[51] Int. Cl.³ ...................... G01R 31/02; G01R 31/08; G01V 3/15
[52] U.S. Cl. ...................................... 324/54; 324/52; 324/71 R; 324/72; 324/365
[58] Field of Search ................... 324/52, 54, 67, 71 R, 324/72, 65 CR, 348, 349, 358, 365, 425, 326

[56] References Cited

U.S. PATENT DOCUMENTS

| | | | |
|---|---|---|---|
| 2,034,447 | 3/1936 | Schlumberger | 324/349 |
| 2,123,545 | 7/1938 | Pearson | 324/348 X |
| 2,345,608 | 4/1944 | Lee | 324/358 |
| 2,872,638 | 2/1959 | Jones | 324/365 |
| 3,526,831 | 9/1970 | Smith | 324/54 |
| 4,078,510 | 3/1978 | Morgan | 324/72 X |
| 4,099,117 | 7/1978 | Erath | 324/52 X |
| 4,228,399 | 10/1980 | Rizzo et al. | 324/365 X |

Primary Examiner—Gerard R. Strecker
Attorney, Agent, or Firm—Brisebois & Kruger

[57] ABSTRACT

This invention relates to monitoring the condition of sheathings which electrically insulate a submarine structure brought to an electrical potential differing from that of the sea water, or to monitoring the operation of the anodes if said pipeline is under cathodic protection.

According to the invention one or more sets of three electrodes, which are spaced apart and aligned parallel to said pipeline, is/are displaced longitudinally above said pipeline, and the difference between the potential of the central one of said electrodes of the or each set and the algebraic sum of the potentials of the other two of said electrodes of the or each set, is measured in continuous fashion.

In carrying out the method there is provided a chassis made of an electrically insulating material which has secured to it one or more sets of three electrodes which are aligned and equidisant, the central one of said electrodes of the or each set being connected to one terminal of an electrical voltage-measuring instrument having two terminals, and the other two of said electrodes of the or each set being connected to the other terminal of said measuring instrument.

4 Claims, 4 Drawing Figures

METHOD OF SURVEYING SUB-SEA PIPELINE

BACKGROUND OF THE INVENTION

The present invention relates to methods and devices for checking the condition of sheathings of metal pipelines, metal cables and other metal structures, all of these being simply referred to as "pipelines" in the following, which are submerged at sea or buried in the sea bed, (hereinafter referred to simply by the adjective "submarine", as well as to monitor the effectiveness of the cathodic protection of such pipelines. Complementarily, the invention may be applied to locate such pipelines provided that they are at a different potential from that of the environment in which they are situated, as is the case if they have cathodic protection. If this is not the case, they are brought to a different potential from that of the environment, so that the invention may be applied.

The invention is applicable, for example, to metal pipelines used for conveying liquid or gaseous hydrocarbons, which are laid on the bottom or embedded in the sea bed. The cathodic protection of such pipelines against corrosion is established, on the one hand, by means of evenly spaced zinc rings which form anodes, and on the other hand by means of an electrically insulating sheathing which prevents or at least restricts electrical exchanges between the pipeline and the environment, in such manner that the anode does not play any part or a small part only, if the sheathing is in good condition.

It is clearly essential for the operation of the anodes and the condition of the sheathing to be checked periodically. In practice however, it is difficult and occasionally impossible to entrust divers—even if they are equipped with improved instruments—with the task of performing a detailed inspection of the operation of the anodes and of the condition of the sheathings, since the depth of the water, the possible embedment and the very length of the pipelines which may reach several hundred kilometers, frequently represent grave or insurmountable obstacles. The trend consequently consists in making use of manned or remotely controlled craft which render it possible to establish continuous reports rapidly.

Some methods in use at present consist, for example, in measuring the electric current flows circulating in the sea water close to the anodes and sheathings, or else in determining the local variations of electrical fields, but these methods and devices are not genuinely reliable, because the quantities measured are not sufficiently representative and thus their interpretation is inaccurate.

It is an object of the invention to minimize or eliminate these disadvantages by evaluating the evolution of the differences in electrical potential between electrodes close to the pipelines when this array of electrodes has imposed on it a translatory displacement parallel to the bottom and more particularly parallel to the pipeline.

As a matter of fact, these differences in potential derive on the one hand from the exchanges of electric currents between the sea water and the pipeline which are a function of the condition of the sheathing, and on the other hand from the exchanges between the sea water and the anodes which are a function of the operation of these latter. Consequently, if it is observed that these differences in potential remain constant or rise a little upon approaching an anode, this leads to the conclusion that this latter does not operate or operates badly; if it is observed that they rise rapidly in an area comparatively distant from an anode, this leads to the conclusion that the sheathing is in poor condition.

In practice, each potential gradient may correspond not only to the current exchange investigated, but also to the circulation of electric currents extraneous to the system in question (stray currents, earth currents, etc . . . ).

To avert evaluation errors, the effects of the two electrical fields one of which originates from the system in question (being the pipeline which is to be checked, as it happens), and the other from random sources, should consequently be separated. This is why the invention is based on the application of differential measurements intended to eliminate any signal generated by an electrical field extraneous to the system in question.

SUMMARY OF THE INVENTION

Accordingly, the invention consists in a method for monitoring the condition of sheathings which electrically insulate a submarine structure brought to an electrical potential differing from that of the sea water, or for monitoring the operation of the anodes if said pipeline is under cathodic protection, wherein a set of three electrodes which are spaced apart and aligned parallel to said pipeline is displaced longitudinally above said pipeline, and the difference between the potential of the central one of said electrodes and the algebraic sum of the potentials of the other two of said electrodes, is measured in continuous fashion.

The invention also consists in a device for carrying out the method which comprises a chassis made of an electrically insulating material, which may be displaced within the sea water, and which has secured to it one or more sets of three preferably equidistant and aligned electrodes, the two outer electrodes of which are connected to the same terminal of an electrical voltage-measuring instrument such as a millivoltmeter, and the central electrode of which is connected to the other terminal of said measuring instrument.

BRIEF DESCRIPTION OF THE DRAWINGS

In order that the invention may be more clearly understood, reference will now be made to the accompanying drawings which show certain embodiments thereof by way of example and in which.

DETAILED DESCRIPTION OF PREFERRED EMBODIMENTS

Figure 1:
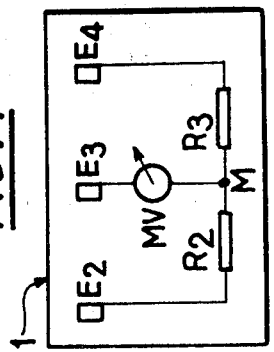
FIG. 1 is a block diagram of a device according to the invention.

Referring now to the drawings, FIG. 1 is a block diagram of one embodiment of device. A chassis 1 of an electrically non-conductive material, for example a glass-epoxy laminate, has secured to it the three identical electrodes E2, E3, E4 which are substantially in alignment. The central electrode E3 is practically equidistant from the outer electrodes E2 and E4 which are separated from each other by a distance which may vary as a function of the diameter of the pipeline and which is commonly of the order of 2 to 3 meters, so that the device may have a satisfactory sensitivity.

The nature of the electrodes is not affected by the invention; they may be of any known type, preferably non-polarisable, for example of the silver/silver chloride type, like those widely applied for potential measurements at sea. The two outer electrodes E2 and E4 are connected to the same terminal M of a millivoltmeter MV and the central electrode E3 is connected to the other terminal of the millivoltmeter; resistors R2 and R3 are connected between the terminal M of the millivoltmeter MV and the electrodes E2 and E4, and the ohmic values of said resistors are such that the intensity of the electric currents is low; for example, if the electrodes have an inherent resistance of 10 ohms, the resistors R2 and R3 may be rated at 500,000 ohms each, and the millivoltmeter MV may have a resistance of 20 megohms. The difference in potential V between M and the electrode E3 indicated by the millivoltmeter MV is equal to the difference between the potentials of the electrode E2 and E4:

$$V = VE3 - (VE2 + VE4)/2$$

The millivoltmeter MV constantly indicates the difference in potential between the terminal M and the central electrode E3. It may be installed on the chassis 1 and be of the recording type or may transmit signals intercepted on shore or aboard ship; it may also be installed on board a ship and be connected to the electrode E3 and the electrodes E2 and E4 by means of flexible leads. The device used to ascertain the difference in potential between M and the electrode E3 depends on the conditions in which the monitoring operation is performed.

If there are electric currents which, like earth or stray currents, are of an origin extraneous to the system—that is to say to the pipeline and to the anodes, they cause identical modifications of the potentials VE2, VE3 and VE4, and the difference V remains the same; the indications given by the millivoltmeter MV are consequently unaffected by the electric currents extraneous to the system which is to be monitored.

Figure 2:
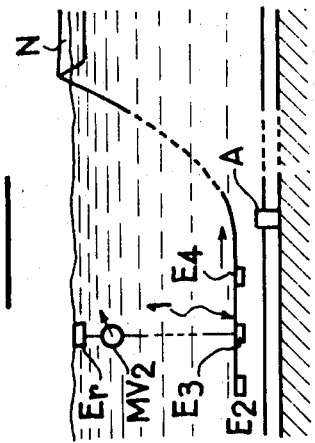
FIG. 2 is a diagram indicating the device of FIG. 1 in use.

The device described above may be applied to check on the cathodic protection of a pipeline laid on the sea bottom or buried in the sea bed. To this end, as depicted in FIG. 2, the device of FIG. 1 is displaced longitudinally above a pipeline at a distance of 2 to 3 meters, approximately, with its electrodes facing towards the bottom. Upon entering the areas in which the electric field engendered by each anode A of the pipeline is adequate to act in appreciable manner on the electrodes E2, E3 and E4, this field increases, reaches a maximum abreast of the anode and then diminishes until it becomes negligible. When the device of FIG. 1 is displaced in the direction of the arrow, the electrode E4 is the first to be affected by this field, followed by the electrodes E3 and E2; this results in the appearance of a difference in potential, initially between E4 and E3 and then between E2 and E3.

Figure 3:
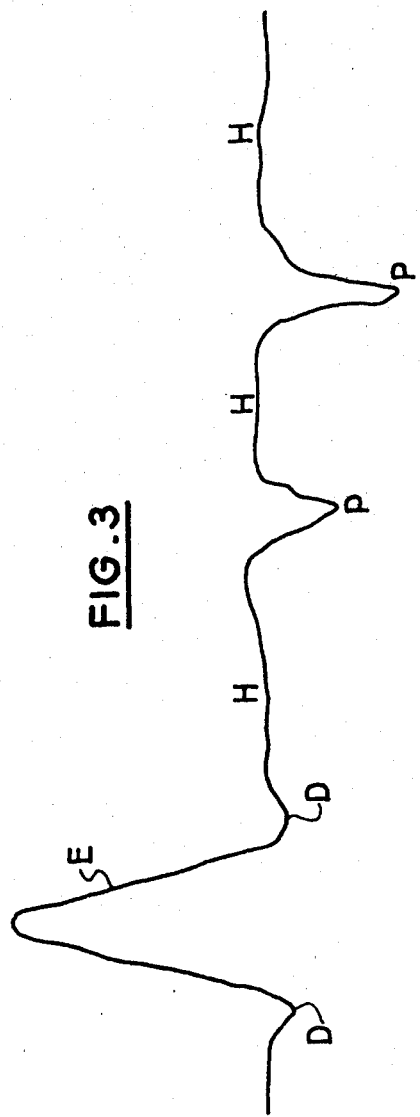

The graph recorded by the millivoltmeter MV whilst passing over the anode is shown at the left of the graph of FIG. 3. When the electrodes of the device are outside the field of the anode, they are at the same potential and the corresponding graph is flat. The gradual penetration of the set of 3 electrodes into the electric field corresponds to the portion D of the graph, having an upwardly facing concavity. The portion E having a downwardly facing concavity has a pronounced peak corresponding to the central electrode E3 passing through the maximum field area, that is to say precisely positioned above the anode (the two electrodes E2 and E4 are then both at lower potentials than the electrode E3). The maximum of FIG. 3 is the higher the greater the intensity of the electric field engendered by the anode A; consequently, it renders it possible to evaluate the operation of the anode. If the displacement of the device is continued, the portion E of the graph diminishes and becomes level again after a sag D which corresponds to departure from the field of the anode.

The device of FIG. 1 applied in accordance with the layout of FIG. 2 equally renders it possible to monitor the condition of the sheathing of the pipeline. As a matter of fact, at the points at which this electrical insulator is in poor condition, the pipeline exchanges an electric current with the sea water: this is made manifest by the peaks P in FIG. 3 having an upwardly facing concavity; in exchange, the graph is almost flat at the points at which the sheathing is in satisfactory condition: these are the portions H of the graph of FIG. 3.

The same device, upon being displaced at right angles to the pipeline, renders it possible to locate the same precisely if it exchanges electric currents with the sea water, even if it is embedded. As a matter of fact, when the device of FIG. 1 passes over this pipeline, the potential of the electrodes E2, E3 and E4 is modified and the millivoltmeter MV records a graph analogous to that of FIG. 3, but with an upwardly facing concavity, the peak of which corresponds to the central electrode E3 passing over the pipeline.

As illustrated in FIG. 2, it is possible to position a reference electrode Er comparatively far from the pipeline, for example close to the surface and, by means of a millivoltmeter MV2, to measure the difference in potential between this reference electrode and one of the electrodes E2, E3, or E4, in such manner as to be apprised of the potential of the pipeline and consequently as to ascertain whether the cathodic protection is adequated or not.

Figure 4:
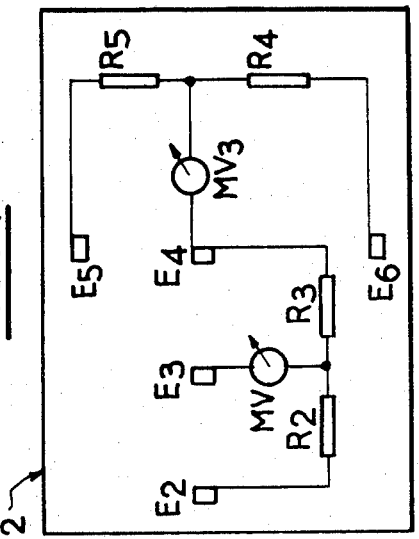
FIG. 3 is a graph made from the readings of the voltage measuring instrument and FIG. 4 is a block diagram of another embodiment of device.

FIG. 4 is a block diagram of another embodiment of device, in which a chassis 2 of an electrically insulating material carries not only the set of three electrodes E2, E3 and E4 of FIG. 1, connected in the same manner to the millivoltmeter MV, but also another set of three electrodes which is identical and at right angles to the first, and the central electrode of which is aligned with the electrodes E2, E3 and E4, is the electrode E4 being common as shown; the central electrode of this latter set is connected to one terminal of a millivoltmeter MV3 the second terminal of which is connected to the two outer electrodes E5 and E6 via the respective resistors R5 and R6. Actually, any one of the electrodes of the first set may be used as the central electrode of the latter set; thus in the case of FIG. 4, the second set is formed by the electrodes E5, E4 and E6, but this is only an example.

This device may be utilized like the device of FIG. 1 by being displaced parallel to the pipeline. For example, if the set of electrodes E2, E3, E4 is parallel to the pipeline, the indications of the corresponding millivoltmeter MV will be useful in providing data on the operation of the anodes as has been stated in the foregoing, and the indications provided by the set of three electrodes E4, E5, E6 are compared to those provided by the set of three electrodes E2, E3, E4 for a clearer understanding of the condition of the sheathings and the effectiveness of the cathodic protection.

Instead of positioning two sets of three electrodes at right angles, it would be possible to install any desired number of sets of three electrodes in such manner as to be evenly distributed in a plane and as to have a common intersection.

Each anode A takes the form of a zinc ring and all the anodes are equidistantly spaced.

I claim:

1. A method for monitoring the condition of sheathings which electrically insulate a submarine pipeline in sea water, or for monitoring the operation of the anodes if said pipeline is under cathodic protection, said pipeline having an electrical potential differing from that of the sea water, said potential being proportional to the natural currents captured by the pipeline from the sea water at defective points in the insulating sheathing of the pipeline, or the natural currents emitted by the pipeline into the sea water by anodes, if said pipeline is under cathodic protection, said method comprises providing a set of three spaced apart substantially aligned electrodes, continuously displacing said set along said pipeline with said electrodes above and in generally aligned parallel relation to the pipeline, and continuously measuring the difference between the potential of the central one of said electrodes and the algebraic sum of the potentials of the other two of said electrodes to provide an indication of the natural currents captured or emitted by the pipeline.

2. A method according to claim 1 wherein the set of electrodes is displaced longitudinally and continuously by displacing a set of three aligned electrodes secured on a chassis of electrically insulating material, and the difference between the potential of the central electrode and the algebraic sum of the potential of the other two electrodes is measured by measuring the difference with an electrical voltage measuring instrument by connecting the central electrode to a first terminal of the instrument, and the other two electrodes of the set to the second terminal of the instrument.

3. A method for monitoring the condition of sheathings which electrically insulate a submarine pipeline in sea water, said pipeline having an electrical potential differing from that of the sea water, or for monitoring the operation of the anodes if said pipeline is under cathodic protection, said method comprising providing a set of three spaced apart substantially aligned electrodes, continuously displacing said set along and above the pipeline while maintaining the electrodes of the set aligned generally parallel with the pipeline, continuously measuring the difference between the potential of the central one of said electrodes and the algebraic sum of the potentials of the other two of said electrodes, providing a second set of three spaced apart aligned electrodes, continuously displacing said second set along and above the pipeline at the same time as said first set while maintaining said second set aligned transversely with respect to said pipeline and said three electrodes of said first set, and continuously measuring the difference between the potential of the central one of said electrodes and the algebraic sum of the potentials of the other two of said electrodes of said second set.

4. A method according to claim 1, wherein the difference in potential between an electrode being displaced close to said pipeline and an electrode being displaced close to the surface is measured simultaneously in continuous fashion.

* * * * *